United States Patent [19]

McPhee

[11] Patent Number: 4,484,916

[45] Date of Patent: Nov. 27, 1984

[54] MEDICAL SOLUTION CONTAINER AND PORT CONSTRUCTION

[75] Inventor: Charles J. McPhee, Huntington Beach, Calif.

[73] Assignee: American Hospital Supply Corporation, Evanston, Ill.

[21] Appl. No.: 340,899

[22] Filed: Jan. 20, 1982

[51] Int. Cl.$^3$ .............................................. A61M 5/00

[52] U.S. Cl. .................................... 604/256; 215/249; 215/251; 215/355; 604/415

[58] Field of Search ........................ 604/256, 408, 415; 215/247, 249, 251, 355; 383/80, 81, 96; 222/81, 89, 541; 141/311 R, 329, 330

[56] References Cited

U.S. PATENT DOCUMENTS

| | | | |
|---|---|---|---|
| 2,626,776 | 1/1953 | Martineau | 251/167 |
| 2,721,552 | 10/1955 | Nosik | 222/81 |
| 2,916,174 | 12/1959 | Orr | 215/43 |
| 3,304,977 | 2/1967 | Hammons | 150/1 |
| 3,343,699 | 9/1967 | Nicko | 215/247 |
| 3,364,930 | 1/1968 | Ryan | 128/214 |
| 3,519,158 | 7/1970 | Anderson | 215/37 |
| 3,788,374 | 1/1974 | Saijo | 150/1 |
| 3,904,059 | 9/1975 | Bellamy et al. | 215/249 |
| 3,917,100 | 11/1975 | Dukess | 215/329 |
| 3,986,507 | 10/1976 | Watt | 128/214 |
| 4,049,033 | 9/1977 | Ralston, Jr. | 105/5 |
| 4,098,422 | 7/1978 | Slomski | 215/355 |
| 4,136,694 | 1/1979 | Kuehn | 128/214 |
| 4,140,162 | 2/1979 | Gajewski et al. | 150/1 |
| 4,170,994 | 10/1979 | Komatsu | 128/214 |
| 4,191,231 | 3/1980 | Winchell et al. | 150/8 |
| 4,243,150 | 1/1981 | Gunne et al. | 215/247 |
| 4,254,884 | 3/1981 | Maruyama | 215/247 |
| 4,303,067 | 12/1981 | Connolly et al. | 604/408 |
| 4,393,909 | 7/1983 | Pearson | 150/8 |

*Primary Examiner*—C. Fred Rosenbaum
*Assistant Examiner*—J. L. Kruter
*Attorney, Agent, or Firm*—Tilton, Fallon, Lungmus

[57] ABSTRACT

Improved port and closure constructions are disclosed for medical solution containers, particularly collapsible containers intended for storing and administering parenteral solutions. An outlet port includes a tubular neck with an elastomeric sealing disc held against the distal end of the neck by a tear-off cap, the disc having planar surfaces and a circumferential rib spaced from each of those surfaces for sealingly engaging the inside of the cap. Within the outlet port is an annular collar that slopes and tapers distally inwardly for engaging the spike of an administration set. An inlet port is also provided, such inlet port having a neck with an internal annular distally-facing shoulder and a plurality of longitudinal internal ribs located distal to the shoulder. The ribs are useful for guiding a stopper into sealing engagement with the shoulder without interfering with the seal as so formed.

27 Claims, 13 Drawing Figures

MEDICAL SOLUTION CONTAINER AND PORT CONSTRUCTION

BACKGROUND AND SUMMARY

Collapsible containers for the administration of medical solutions are well known and are disclosed, by way of example, in U.S. Pat. Nos. 3,519,158, 4,140,162, 4,170,994, 4,136,694, 3,986,507, 3,304,977, 3,788,374, 3,364,930, 4,191,231, and 4,049,033. Typically, such a container when used for the storage and administration of parenteral fluids, has an inlet port as well as an outlet port. The outlet port is intended to be coupled to an administration set and is therefore commonly referred to as the administration or set port, whereas the inlet port is designed to permit the injection of therapeutic agents and nutrients into the partially prefilled container and is sometimes identified as the med port. Such a container may contain a partial filling of a sterile solution such as saline or dextrose to function as a diluent for the injected additive. The diluted drug or nutrient is then administered to a patient by means of the administration set which may be either directly or indirectly (i.e., through another parenteral solution set) coupled to the patient.

Maintaining the sterility of the fluid to be administered is clearly of major importance. It has been found, however, that careless or inattentive handling of a parenteral solution container, as the connections are being made for fluid administration or additive introduction through the respective outlet and inlet ports, may create significant risks of contamination. Such risks may be increased where emergency situations are presented that require quick manipulation of the various components, or where extended storage conditions causes components to stick together or to separate in a manner differently than intended. For example, a conventional administration port is often sealed by a soft rubber sealing disc held in place by a thin metal tear-off cap. Should the disc remain in place upon the neck of the container after the cap is removed, a user attempting to remove the disc might inadvertently touch and contaminate the sterile end surface of the neck, and such contamination may then be transferred to the contents of the container when the spike of the administration set is later plugged into the outlet port.

It is therefore an object to provide a container for medical solutions having improved inlet and outlet port constructions to reduce possibilities of contamination during storage and use, improve the ease of handling such a container when fluids are to be withdrawn or introduced and, at the same time, increase the ease and efficiency by which such a container may be manufactured. Since such containers are discarded following use, greater efficiencies in production resulting from improvements in construction tend to benefit patients in terms of both greater safety and lower cost.

In brief, the medical solution container of this invention may take the form of a collapsible bag having inlet and outlet ports. Each port has a tubular neck enclosed at its end by a metal cap. In the case of the outlet or administration port, a sealing disc or liner of soft elastomeric material is interposed between the end surface of the neck and the tear-off metal cap. The disc has planar surfaces and is provided with an integral circumferentially-extending rib projecting outwardly from its side surface. Ideally, the rib is spaced equal distances from the planar faces and has a diameter (in an undeformed state) greater than the inside diameter of the cap. Specifically, the rib should have a radial dimension less than half distance between each of the planar faces of the disc, and should have an axial dimension within the range of about 15 to 30% of the thickness of the disc. When the parts are assembled, the rib engages the inside surface of the cap and may be deformed thereby without, at the same time, causing any significant deformation of the disc's planar surface in sealing engagement with the end surface of the neck. Because of the frictional engagement between the disc and cap, the disc tends to be removed as the cap is torn away from the neck; however, should the disc happen to remain upon the neck after the cap is removed, the outwardly-projecting rib may be easily gripped or engaged by the fingers, and the disc may be lifted from the neck, without contacting and contaminating the sterile end surface of the neck.

The neck of the outlet port includes a tapered annular collar disposed within the neck and formed integrally therewith for slidably and sealingly engaging the hollow spike of an administration set. The opening defined by the collar (when the collar is unstretched) is smaller than the reduced portion of the bore adjacent thereto, thereby helping to assure effective contact between the collar and the inserted spike. The neck also includes an integral membrane adapted to be pierced by the spike, with the portion of the bore directly beneath (or proximal to) the membrane being of larger diameter to accommodate material of the membrane when such membrane is pierced, deformed, and displaced by the spike.

It has been found that a highly effective tapered annular collar may be formed in a simple molding operation if the distal wall portion of the neck is provided with an enlarged bore to accommodate outward flexing or stretching of the collar as the mold section is withdrawn, and if the inner and outer surfaces of the collar slope inwardly and distally (at an angle of about 5° to 15° measured internally) with the outer surface having a greater acute angle of slope (measured from a line extending in an axial direction). The differential between the angles of slope of the inner and outer surfaces should be within the range of 3° to 10° with a preferred differential being about 5°.

The tubular neck of the inlet or medication port has an internal annular shoulder facing the open distal end of the neck and is also provided with a plurality of longitudinal ribs projecting inwardly from the surface of the bore above (distal to) the shoulder. The ribs serve to guide the body of an elastomeric stopper into sealing engagement with the shoulder while themselves making only limited engagement so as to avoid possibilities of interference with the formation of an effective end seal between the stopper and shoulder. Since the seal occurs at the end of the stopper, contact between the fluid contents of the container and the elastomeric material of the stopper is more limited than in prior constructions, a factor that may be of some significance depending in part on the nature of the contents and the composition of the stopper.

Other important advantages, objects, and features of the invention will become apparent from the specification and drawings.

DRAWINGS

DETAILED DESCRIPTION

Figure 1:
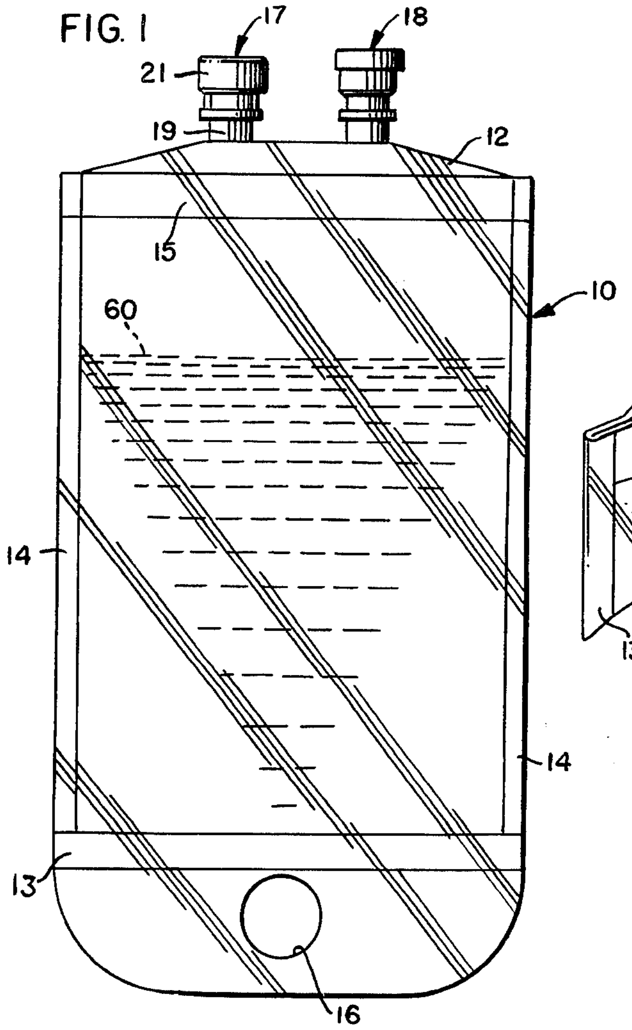
FIG. 1 is a side elevational view of a medical solution container embodying the invention.
Figure 2:
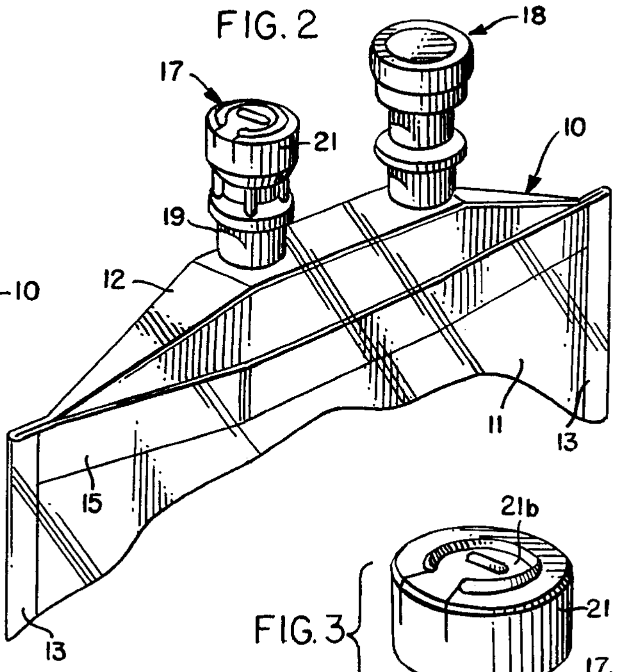
FIG. 2 is a perspective view of the container showing the port assemblies thereof.

Referring to FIGS. 1 and 2 of the drawings, the numeral 10 generally designates a medical solution container in the form of a collapsible bag or pouch 11 and a molded header 12 formed of thermoplastic material. Any suitable thermoplastic material or materials may be used that have the desired properties of flexibility, durability, autoclavability, and inertness. Effective results have been obtained with polyolefins, particularly with propylene-ethylene copolymers.

In the embodiment illustrated, bag 11 is composed essentially of two sheets or films of thermoplastic material heat sealed to each other along their bottom and side marginal areas 13 and 14, respectively, and heat sealed to header 12 along their top marginal areas 15. The bottom end of the bag is provided with an opening 16 to facilitate suspension of the container from the hook of a conventional IV stand. A pair of port assemblies 17 and 18 project from header 12 for the introduction and removal of fluids from the container.

Outlet port assembly 17 may also be referred to as a set port because it is intended to be used to couple the container 10 to a conventional administration set (not shown). As is well known, such a set includes a hollow spike that would be inserted into the neck of the outlet port after the tear-off cap and sealing disc are removed. Such a spike is frictionally retained by the neck so that when the container 10 is inverted and suspended, the fluid contents may be withdrawn therefrom and administered intravenously to a patient at predetermined rates. The three essential components of the outlet port assembly 17 are depicted most clearly in FIGS. 3 and 4 and consist of an outlet port neck 19, a sealing disc 20, and a tear-off cap 21.

Figure 10:
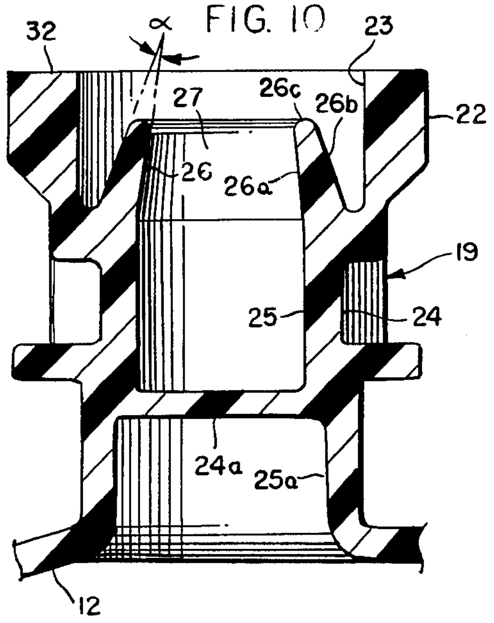

The tubular neck 19 is formed integrally with header 12 and includes a distal wall portion 22 with an enlarged cylindrical bore 23 and a proximal wall portion 24 defining a reduced coaxial cylindrical bore 25. A tapered annular collar 26 is disposed within the neck and is formed integrally therewith, the collar extending distally from the proximal wall portion 25 into the enlarged bore 23. It will be observed from FIGS. 4 and 10 that the collar 26 has an inner surface **26*a* merging proximally with the surface of the reduced cylindrical bore 25, and also has an outer surface 26*b* spaced inwardly from the surface of enlarged cylindrical bore 23. Both the inner surface 26*a* and the outer surface 26*b* slope inwardly and distally, terminating in rounded end surfaces 26*c* that define an opening 27 at the collar's distal end that has a smaller diameter than that of reduced cylindrical bore 25. Consequently, an administration set spike (not shown) having an outside diameter smaller than bore 25 but larger than opening 27 will sealingly engage collar 26** to cause limited expansion of the resilient collar, and will be retained at least in part by the tensioning of the collar about the spike.

The angle of taper of the collar's inner surface **26*a* is shown to be approximately 10° measured from the axis of the neck, although a greater or smaller angle may be provided depending in part on other factors such as the relative length of the collar. In general, inner surface 26*a* would ordinarily have a slope within the range of about 5° to 15°. Of particular significance, however, is the angular differential $\alpha$ between inner surface 26*a* and outer surface 26*b***. The outer surface should have a greater acute angle of slope, the differential $\alpha$ between the angles of slope of the inner and outer surfaces falling within the general range of 3° to 10°. In the preferred embodiment depicted in the drawings, the differential $\alpha$ is approximately 5°.

Figure 7:
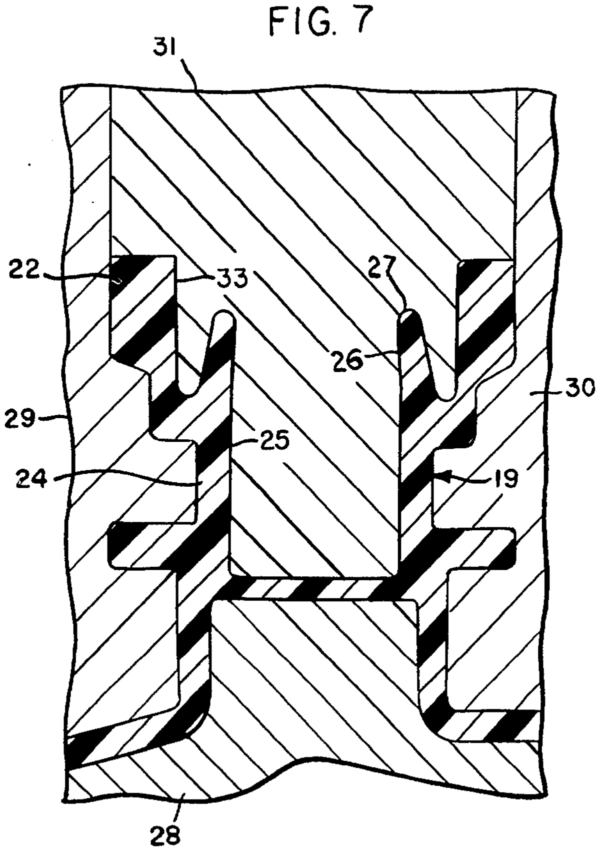
FIGS. 7–10 depict successive steps in the method of molding the outlet port.
Figure 8:
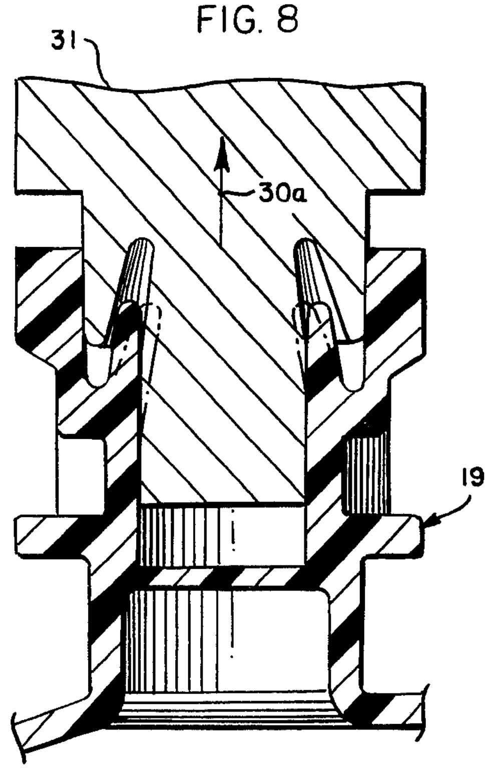
Figure 9:
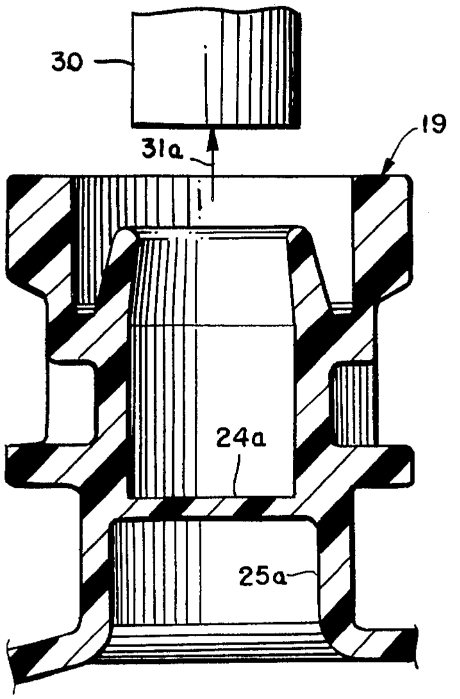

While the angular differential is believed advantageous because it promotes a more effective flexing, wiping, and sealing action of the collar against the outer surface of the spike, it is particularly important because it greatly simplifies the molding of the neck 19 and integral header 12. FIGS. 7–9 depict in somewhat schematic form the sequence of molding steps. Four mold sections 28–31 are shown, the latter being in the form of a pin that is retracted in the direction of arrow **31*a* after sections 28, 29 and 30 have separated and the part 19 is to be stripped from the pin. Since the opening 27 at the reduced end of the collar is smaller than bore 25, separation of the part 19 and pin 31 will necessarily cause enlargement or outward flexing of the wall of the collar. Such outward flexing is illustrated in FIG. 8 and is accommodated without interference from the core pin only because of the angular differential $\alpha$ which provides progressively increasing clearance for such flexure as the core pin separates from the neck. Once separation is complete, the flexible collar returns to its original molded configuration (FIG. 9). The collar construction, and specifically the angular differential between the inner and outer surfaces 26*a* and 26*b* of the collar 26, therefore permit a molding operation utilizing the advantages of core pin separation as shown while, at the same time, providing an outlet port neck having a reduced opening 27** for insuring effective sealing engagement with an administration set spike when the container is used.

The tubular neck 19 includes a pierceable-diaphragm **24*a* formed integrally with proximal wall portion 24 and extending across the reduced cylindrical bore 25. It will be observed that the portion 25*a* of the bore below (on the proximal side of) diaphragm 24*a* has a diameter substantially larger than the portion of the bore immediately above (distal to) that diaphragm. As a spike pierces diaphragm 24*a*, the material of the diaphragm tends to fold or roll downwardly and outwardly, and such displaced material is accommodated in the space afforded by the greater diameter of bore portion 25*a*. The extent of relief provided will depend on the diameter of the neck and the thickness of diaphragm 24*a*; however, the relief for any given construction should be just enough to accommodate the displaced material of the diaphragm while at the same time limiting the extent of lateral displacement, and bracing the displaced material of the diaphragm, so that a snug frictional seal is formed about the spike and the displaced material of the pierced diaphragm. Thus, in use of the container, two sealing areas are formed to prevent leakage and secure the spike in place: one between the spike and the stretched collar 26 at opening 27, and the other between the spike and the annulus of displaced diaphragm material within bore portion 25***a*.

Figure 3:
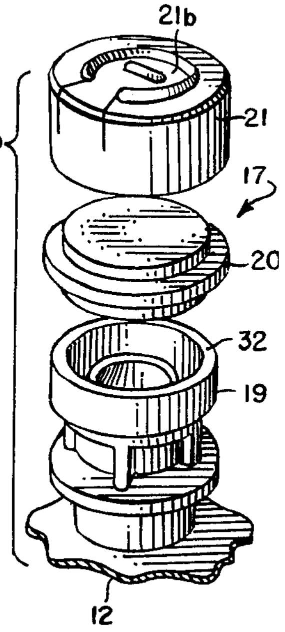
FIG. 3 is an enlarged exploded perspective view illustrating the components of the outlet port assembly.
Figure 4:
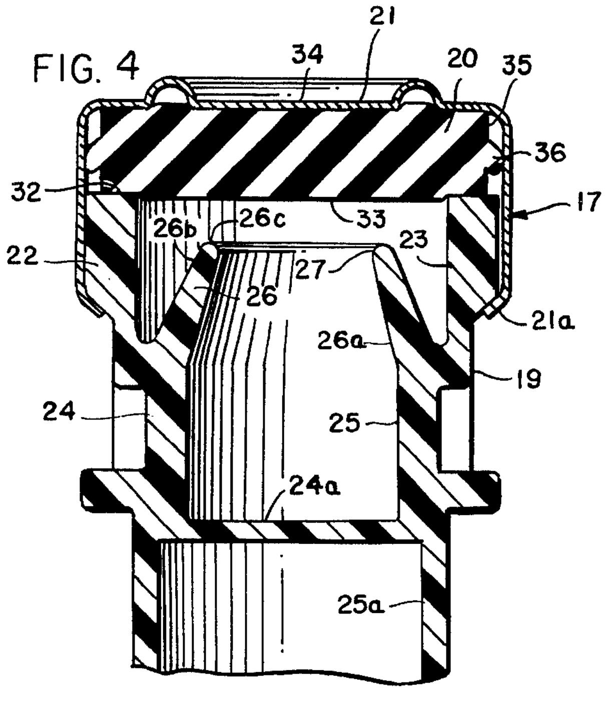
FIG. 4 is a further enlarged longitudinal sectional view of the outlet port assembly.

The tubular neck 19 terminates at its distal end in a planar annular end surface 32. As revealed in FIGS. 3–5, that end surface is engaged by one of the faces 33 of resilient sealing disc 20. The opposite face 34 of the disc is engaged by tear-off cap 21. The cap itself is entirely conventional, may be formed of aluminum or any other relatively soft metallic or polymeric material, has its annular edge 21*a* swaged inwardly to secure it to neck 19 with the sealing disc 20 in a slightly compressed condition as shown in FIG. 4 (the cap as shown in FIG. 3 is un-swaged as it would appear prior to assembly of the parts), and has a disc-shaped central section 21*b* that is partially cut free from the cap and may be pried upwardly by a user and then pulled outwardly to tear the cylindrical wall portion of the cap and thereby cause separation of the cap from the remaining elements.

Figure 6:
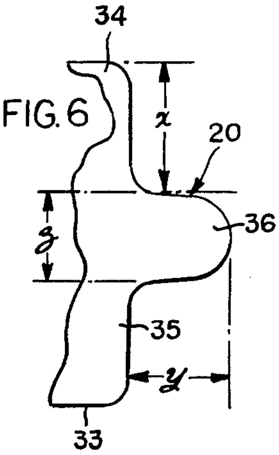
FIG. 6 is a fragmentary view of the longitudinal outline of the sealing disc illustrating the dimensional relationships of structural features thereof.
Figure 5:
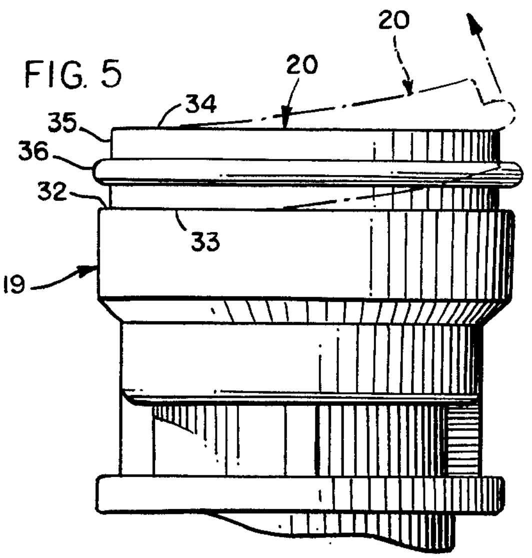
FIG. 5 is an elevational view showing the outlet port assembly after the tear-off cap has been removed therefrom, and further illustrating, in broken lines, the step of peeling away the elastomeric sealing disc.

Sealing disc 20 has a generally cylindrical side surface 35 with an integral annular rib 36 projecting outwardly and circumferentially therefrom. As illustrated in FIGS. 5 and 6, the rib is spaced equal distances x from each of the faces 33 and 34. In an undeformed state, the rib has a diameter appreciably larger than the outside diameter of neck 19 adjacent surface 32, and sufficiently larger than the inside diameter of the cap to cause deformation of the rib when the sealing disc is disposed within the cap (FIG. 4). In addition, the rib, which preferably has a rounded periphery when viewed in elevation, has a radial dimension y less than the distance x between the rib and each of the faces 33, 34, and has an axial dimension z within the general range of 15 to 30% of the total thickness of the disc (2x plus z). In the illustrated embodiment, the axial distance z is approximately 18 to 20% of the disc's total thickness.

Such a construction yields a number of important advantages. The deformation of the rib when the disc is inserted into cap 21 causes the rib to function as a centering and retaining means tending to hold the disc in place within the cap; however, because of the relationships described, rib 36 is incapable of flexing downwardly (proximally) a distance sufficient to contact the end surface 32 of the neck 19 and possibly interfere with the formation of an effective seal between surface 32 and planar face 33 of the disc. Following removal of the tear-off cap, disc 20 may tend to cling or adhere to surface 32, as illustrated in FIG. 5. In that event, a user may easily lift the disc free from surface 32 by prying a portion of rib 36 upwardly (distally) as shown in broken lines in FIG. 5. Such prying action, using the index finger and lifting a portion of the rib away from neck 19, is readily accomplished without contacting end surface 32 and the surface of enlarged bore 23 because the rib is spaced a substantial distance from surface 32 and has a diameter greater than neck 19 (FIG. 5). Since the rib is equidistant from planar faces 33 and 34, the sealing disc 20 may be inserted into cap 21 in either of two ways (i.e., with faces 33 and 34 being reversible in position), thereby facilitating production assembly of the container.

In the preferred embodiment of the invention, sealing disc 20 is formed of natural rubber; however, any other relatively soft elastomeric material may be used that would be effective in providing a resilient seal in the manner described above. Also, while the drawings illustrate what is regarded as a particularly effective form of disc construction in which the rib extends continuously about the disc, it is believed that at least some of the functions and results described above might be achieved if the rib were discontinuous, that is, interrupted at one or more circumferential locations.

Figure 12:
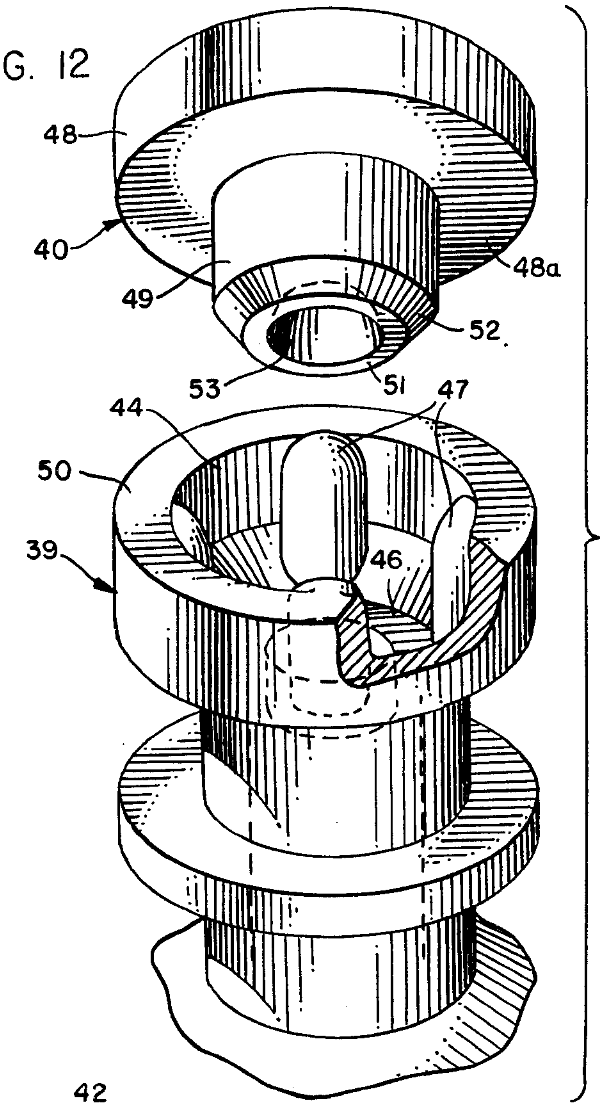
FIG. 12 is an enlarged perspective view of the neck and stopper elements of the inlet port assembly.
Figure 13:
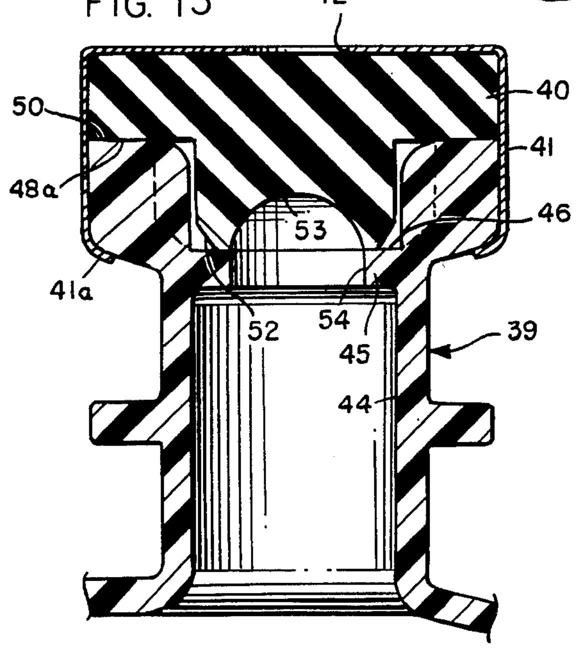
FIG. 13 is a longitudinal sectional view showing the cooperative relationship between the inlet port neck and the piercable stopper.
Figure 11:
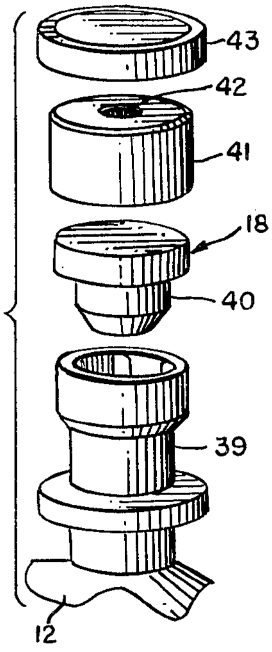
FIG. 11 is an exploded perspective view illustrating components of the inlet port assembly.

The inlet port assembly 18 is shown in detail in FIGS. 11–13 and includes tubular neck 39 formed integrally with header 12, stopper 40, and retention cap 41. Like cap 21, retention cap 41 may be formed of aluminum and is swaged along its periphery 41*a* to secure it to neck 39; however, cap 41 differs by being non-removable and having a central opening 42 in its top surface so that an axial portion of stopper 40 is exposed for needle insertion. To avoid contamination of the surface of the stopper exposed by opening 42, a suitable cover 43 formed of plastic or other material may be removably affixed to the cap 41. Since the cover and its method of attachment to the cap form no part of this invention, and since various means might be used to provide such attachment, all within the scope of the prior art, the cap and its mounting will not be described in further detail herein.

Neck 39 has a bore 44 extending therethrough. Within the bore is an annular projection 45 formed integrally with the wall of the neck and defining a planar annular upper (distal) surface 46. In the portion of bore 44 above (distal to) shoulder 46 are a plurality of longitudinally-extending circumferentially-spaced ribs 47. It will be observed from FIGS. 12 and 13 that the ribs not only extend distally with respect to shoulder 46 but are also disposed outwardly or laterally beyond that shoulder.

The stopper 40 is of inverted hat-shaped configuration with a head portion 48 and an integral, coaxial body portion 49. The head portion has a diameter generally the same as the outside diameter of the distal end of neck 39. The cylindrical body portion 49 has a diameter less than the diametric spacing between ribs 47, at least when the stopper is in an undeformed or uncompressed state. However, the length of the cylindrical body portion when the stopper is undeformed or uncompressed is slightly greater than the distance between the end surface 50 of the neck and shoulder 46. The free end of body portion 49 is provided with an annular end surface 51. In the embodiment illustrated, body portion 49 has a beveled edge or surface 52 circumscribing annular surface 51, and the central area of body portion 49 is recessed at 53 (FIG. 12).

The result is a construction in which effective sealing occurs in two annular zones. A proximal seal occurs between the annular end surface 51 of the stopper and shoulder 46 of the neck, and a distal seal occurs between the end surface 50 of the neck and the undersurface (or annular proximal surface) 48*a* of head 48. The proximal seal is of particular significance because it prevents the invasion of the liquid contents of the container into the zone extending about the cylindrical surface of body 49. Direct contact between the fluid and the stopper is therefore limited in area to the concave surface of recess 53. The effectiveness of the proximal seal is enhanced by a slightly greater length of body portion 49 (in an undeformed state) relative to the distance between shoulder 46 and surface 50, and by the further fact that a slight clearance is provided between body portion 49 and ribs 47, at least before axial compressive forces are applied to the stopper by cap 41. During an assembly operation, the cap 40 may therefore be fitted into place without encountering resistance from ribs 47 that might interfere with the formation of an effective proximal seal between end surface 51 of the stopper and annular shoulder 46. However, if for any reason the proximal seal should fail, the distal seal between head surface 48*a* and neck surface 50 will serve as a back-up to prevent leakage. Conversely, the distal seal performs a major function in preventing the entry of contaminants into the container; in that regard, the proximal seal serves a secondary or back-up function.

The inlet port assembly is used whenever an additive is to be injected into and mixed with the pre-packaged contents of the container. For that purpose, container 10 is only partially filled with parenteral fluid at the time of manufacture. FIG. 1 illustrates a typical level 60 for the contents of a container designed to hold 100 milliliters of sterile fluid for injection. If medication is to be administered intravenously to the patient, the medicament may be injected into the container through the inlet port, mixed with the diluent already packaged in the container, and administered to the patient through an administration set coupled to outlet port 17. When injecting the medicament into the container, cover 43 is removed and the needle of the syringe (not shown) is simply inserted through cap opening 42 and through resilient self-sealing stopper 40. The stopper may be formed of any suitable elastomeric material; in the embodiment illustrated, a soft natural rubber is utilized for stopper 40 as well as sealing disc 20.

While in the foregoing I have disclosed embodiments of the invention in considerable detail for purposes of illustration, it will be understood by those skilled in the art that many of these details may be varied without departing from the spirit and scope of the invention.

I claim:

1. A medical solution container formed of flexible thermoplastic material having a tubular neck projecting away from said container and defining an outlet portion for receiving and retaining the spike of an administration set, said neck having a proximal end merging with said container and a distal end opposite from said proximal end and remote from said container, said distal end including a distal wall portion providing an enlarged cylindrical bore and said proximal end including a proximal wall portion providing a reduced coaxial cylindrical bore, a tapered annular collar disposed within said neck and formed integrally therewith, said collar extending distally from said proximal wall portion into said enlarged bore, said collar also having an inner surface merging proximally with the surface of said reduced cylindrical bore and having an outer surface spaced inwardly from the surface of said enlarged cylindrical bore, said inner and outer surfaces of said tapered collar both sloping inwardly and distally with said outer surface having a greater acute angle of slope, said neck having an annular sealing surface at its distal end, an elastomeric sealing disc engaging said sealing surface, and a tear-off cap detachably affixed to said neck and retaining said disc in place against said sealing surface, said elastomeric sealing disc having planar faces and a generally cylindrical side surface, said disc also having an integral circumferentially-extending rib projecting outwardly from said surface, said rib being spaced equal distances from said planar faces and having a diameter in an undeformed state greater than the outside diameter of said neck, said tear-off cap retaining said disc with one of the planar faces thereof in liquid-tight sealing engagement with said end surface of said neck, said cap also having an inside surface engaging said rib.

2. The container of claim 1 in which said rib has a radial dimension less than the distance between said rib and each of said planar faces.

3. The container of claims 1 or 2 in which said rib has an axial dimension within the range of 15 to 30% of the thickness of said disc.

4. The container of claim 3 in which said rib has an axial dimension of about 18% of the thickness of said disc.

5. The container of claims 1 or 2 in which said rib has a peripheral surface of rounded cross section.

6. The container of claim 1 in which said disc is formed of soft rubber.

7. A medical solution container formed of thermoplastic material having a tubular neck projecting away from said container, said neck having a bore extending therethrough and having a proximal end merging with said container and an open distal end opposite from said proximal end ane remote from said container, an annular shoulder provided by said neck within said bore facing said open distal end, said neck including a plurality of longitudinal ribs projecting inwardly from the surface of said bore and disposed radially and distally beyond said shoulder, a pierceable resilient stopper having a head portion and an integral cylindrical body portion, said cylindrical body portion being received within said bore distal to said shoulder and having an annular end surface sealingly engaging said shoulder, said container also being provided with a second tubular neck, said second neck terminating in an annular end surface, an elastomeric sealing disc having planar faces and a generally cylindrical side surface, said disc also having an integral circumferentially-extending rib projecting outwardly from said side surface, said rib being spaced equal distances from said planar faces and having a maximum diameter in an undeformed state greater than the outside diameter of said neck, and a tear-off cap detachably affixed to said second neck and retaining said disc with one of said planar faces in liquid-tight sealing engagement with the end surface of said said second neck, said cap also having an inner side surface engaging said circumferentially-extending rib.

8. The container of claim 7 in which said circumferentially-extending rib has a radial dimension less than the distance between said rib and each of said planar faces.

9. The container of claim 7 in which said circumferentially-extending rib has an axial dimension within the range of 15 to 30% of the thickness of said disc.

10. The container of claim 9 in which said axial dimension is about 18% of the thickness of said disc.

11. The container of claim 7 in which said circumferentially-extending rib has a peripheral surface of rounded cross section.

12. The container of claim 7 in which said disc is formed of soft rubber.

13. The container of claim 7 in which said container is in the form of a generally flat collapsible thermoplastic bag having a header extending along one edge thereof, said second neck and said first-mentioned neck being formed integrally with said header.

14. A medical solution container formed of thermoplastic material having a tubular neck projecting away from said container, said neck having a bore extending therethrough and having a proximal end merging with said container and an open distal end opposite from said proximal end and remote from said container, an annular shoulder provided by said neck within said bore facing said open distal end, said neck including a plurality of longitudinal ribs projecting inwardly from the surface of said bore and disposed radially and distally beyond said shoulder, a pierceable resilient stopper having a head portion and an integral cylindrical body portion, said cylindrical body portion being received within said bore distal to said shoulder and having an annular end surface sealingly engaging said shoulder, said container also having a second tubular neck defining an outlet port for receiving and retaining the spike of an administration set, said second neck having a proximal end merging with said container and a distal end opposite from said proximal end and remote from said container, said distal end of said second neck having a distal wall portion providing an enlarged cylindrical bore and said proximal end of said second neck including a proximal wall portion providing a reduced coaxial cylindrical bore, a tapered annular collar disposed within said second neck and formed integrally therewith, said collar extending distally from said proximal wall portion into said enlarged bore, said collar also having an inner surface merging proximally with the surface of said reduced cylindrical bore and having an outer surface spaced inwardly from the surface of said enlarged cylindrical bore, said inner and outer surfaces of said tapered collar both sloping inwardly and distally with said outer surface having a greater acute angle of slope.

15. The container of claim 14 in which the differential between the angles of slope of said inner and outer surfaces of said tapered collar is within the range of 3° to 10°.

16. The container of claim 15 in which said differential is about 5°.

17. The container of claims 14 or 15 in which said inner surface has an angle of slope within the range of 5° to 15° measured from the longitudinal axis of said second neck.

18. The container of claim 17 in which the angle of slope of said inner surface is about 10°.

19. The container of claim 14 in which said second neck is provided with a pierceable diaphragm formed integrally with said proximal wall portion and extending across said reduced cylindrical bore.

20. The container of claim 14 in which said reduced cylindrical bore has portions disposed on opposite sides of said diaphragm, said portion of said bore proximal to said diaphragm having a diameter substantially larger than the portion of said reduced cylindrical bore distal to said diaphragm.

21. The container of claim 14 in which said second neck has an annular sealing surface at its distal end, an elastomeric sealing disc engaging said sealing surface, and a tear-off cap detachably affixed to said second neck and retaining said disc in place against said sealing surface.

22. The container of claim 21 in which said elastomeric sealing disc has plannar faces and a generally cylindrical side surface, said disc also having an integral circumferentially-extending rib projecting outwardly from said surface, said rib being spaced equal distances from said planar faces and having a diameter in an undeformed state greater than the outside diameter of said second neck, and a tear-off cap detachably affixed to said second neck and retaining said disc with one of the planar faces thereof in liquid-tight sealing engagement with said end surface of said second neck, said cap also having an inside surface engaging said circumferentially-extending rib.

23. The container of claim 22 in which said circumferentially-extending rib has a radial dimension less than the distance between said rib and each of said planar faces.

24. The container of claim 22 in which said rib has an axial dimension within the range of 15 to 30% of the thickness of said disc.

25. The container of claim 24 in which said rib has an axial dimension of about 18% of the thickness of said disc.

26. The container of claim 22 in which said circumferentially-extending rib has a peripheral surface of rounded cross section.

27. The container of claim 22 in which said disc is formed of soft rubber.

* * * * *